US006620970B2

(12) United States Patent
Schiffer et al.

(10) Patent No.: US 6,620,970 B2
(45) Date of Patent: Sep. 16, 2003

(54) WORK-UP OF THE AMMOXIMATION PRODUCTS OF KETONES BY LIQUID-LIQUID EXTRACTION IN A TERNARY SOLVENT SYSTEM

(75) Inventors: Thomas Schiffer, Haltern (DE); Peter Ernst Esser, Recklinghausen (DE); Jörg Krissmann, Marl (DE); Martin Roos, Haltern (DE); Günter Stevermüer, Marl (DE); Georg Friedrich Thiele, Hanau (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/232,569

(22) Filed: Sep. 3, 2002

(65) Prior Publication Data

US 2003/0065220 A1 Apr. 3, 2003

(30) Foreign Application Priority Data

Aug. 31, 2001 (DE) .......................... 101 42 621

(51) Int. Cl.⁷ ..................... C07C 249/08; C07C 249/14
(52) U.S. Cl. ...................... 564/264; 564/259; 564/267
(58) Field of Search ................... 564/259, 264, 564/267

(56) References Cited

U.S. PATENT DOCUMENTS

| 4,794,198 A | 12/1988 | Roffia et al. ............... 564/267 |
| 5,227,525 A | 7/1993 | Tonti et al. ................ 564/267 |
| 5,451,701 A | 9/1995 | Zajacek et al. ............. 564/267 |
| 5,498,793 A | 3/1996 | Mantegazza et al. ....... 564/265 |
| 5,637,715 A | 6/1997 | Thiele et al. .............. 569/265 |

FOREIGN PATENT DOCUMENTS

| EP | 0 208 311 | 1/1987 |
| EP | 0 267 362 | 5/1988 |
| EP | 0 299 430 | 1/1989 |
| EP | 0 496 385 | 7/1992 |
| EP | 0 564 040 | 6/1993 |
| EP | 0 735 017 | 2/1996 |
| EP | 0 690 045 | 3/1996 |

*Primary Examiner*—Peter O'Sullivan
(74) *Attorney, Agent, or Firm*—Oblon, Spivak, McClelland, Maier & Neustadt, P.C.

(57) ABSTRACT

The present invention relates to a process for working up an ammoximation reaction mixture, by separating a catalyst from the reaction mixture, removing the ketone oxime product, discharging the water of the reaction, and recirculating a solvent, where the ketone oxime formed is removed in a liquid phase with at least one liquid-liquid extraction in a ternary solvent system.

15 Claims, 2 Drawing Sheets

WORK-UP OF THE AMMOXIMATION PRODUCTS OF KETONES BY LIQUID-LIQUID EXTRACTION IN A TERNARY SOLVENT SYSTEM

BACKGROUND OF THE INVENTION

1. Field of the Invention

The present invention relates to a process of working up ammoximation products of ketones, which have preferably 8 to 20 carbon atoms, by liquid-liquid extraction in a ternary solvent system

2. Discussion of the Background

Ammoximation of alkanones and/or cycloalkanones by hydrogen peroxide and ammonia over heterogeneous catalyst systems have been described. Examples of these systems, which contain at least one of titanium, silicon, or oxygen can be found in EP 0 299 430 (Montedipe), EP 0 564 040 (Enichem) and U.S. Pat. No. 5,637,715 (Degussa).

In general, the catalyst utilized is a microporous or mesoporous titanium zeolite, while titanium silicalite TS1 is commonly employed for the ammoximation reaction. Additional components may be added to the catalyst system for the ammoximation of large and bulky alkanones or cycloalkanones. Accordingly, a cocatalyst catalyst system including amorphous silicates is described in DE 195 21 011 (Enichem), a cocatalyst system including acidic solids is described in DE 100 47 435 (Degussa-Hüls), and a cocatalyst system including ammonium ions is described in DE 101 03 581 (Degussa-Hüls).

DE 100 47 435 and DE 101 03 581 demonstrate that ammoximation of large and bulky (cyclo)alkanones (e.g., cyclododecanone) proceeds quickly and selectively in polar organic solvents that are completely or partly miscible with water. Suitable disclosed organic solvents include short-chain alcohols having from 1 to 6 carbon atoms.

Generally, as has been illustrated for the ammoximation of cyclododecanone (CDON), ammoximation proceeds in two substeps, (1) hydroxylamine formation and (2) oximation. In this process water is first introduced as an aqueous hydrogen peroxide solution and, second, water is formed in stoichiometric amounts as a reaction product in each of the two substeps. Additionally, water is formed in the unproductive decomposition of hydrogen peroxide and hydroxylamine, formally shown in the secondary reactions (3) and (4).

$$NH_3 + H_2O_2 \rightarrow H_2O + NH_2OH \qquad (1)$$

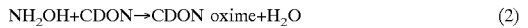

$$NH_2OH + CDON \rightarrow CDON\ oxime + H_2O \qquad (2)$$

$$2NH_2OH + H_2O_2 \rightarrow 4H_2O + N_2 \qquad (3)$$

$$2H_2O_2 \rightarrow 2H_2O + O_2 \qquad (4)$$

As a consequence, the water content of the reaction mixture increases during the reaction. If large alkanones or cycloalkanones are to be ammoximated, the solubility of the corresponding oxime in the reaction mixture decreases sharply with increasing water content.

For this reason, it is particularly desired that the amount of water present during the reaction be limited, particularly in the case of large cycloalkanones. According to DE 100 47 435 and DE 101 03 581, the amount of water may be limited by using ammonia as a dry gas and hydrogen peroxide as a highly concentrated solution (usually ≧30% by weight). It is also advantageous for the starting alcohol to contain no more water than is present in the azeotrope after distillation. However, if the alcohol is to be used a number of times during the reaction process, the water introduced during the reaction has to be separated off again during the work-up.

In most patent applications, the synthesis of the catalyst system, its activation, and the ammoximation reaction are the focus of the investigations. However, the work-up is generally ignored. For example, the abovementioned documents make the general statement that the usually pulverulent catalyst (i.e., a titanium silicalite) is separated off by a filter or a pressure filter. Subsequently, conversions and selectivities are determined by GC analysis and the peroxide consumption is determined directly by redox titration of the reaction solution.

ARCO Chemical Technology describes a multistage synthesis process in EP 0 690 045 and EP 0 735 017. In these references, hydrogen peroxide is formed by first reacting isopropanol with oxygen. After the acetone that is formed has been separated off and hydrogenated, hydrogen peroxide is used in conjunction with ammonia to effect the ammoximation of cyclohexanone, followed by the Beckmann rearrangement to caprolactam. For the process step of ammoximation of cyclohexanone, many work-up methods have been claimed in EP 0 690 045 and EP 0 735 017. Among the possibilities mentioned are distillation and extraction; however, the effectiveness of these techniques has not been demonstrated, as these two methods are not supported by experimental data or examples.

Complete separation of solvent, starting material, and final product by distillation, as described in U.S. Pat. No. 5,451,701 (corresponding to EP 0 690 045 (Arco Chemical Technologies)), may still be possible in the case of cyclohexanone oxime. After removal of the solvent and water by distillation, cyclohexanone (b.p. 155° C./1013 mbar) and cyclohexanone oxime (b.p. 206–210° C./1013 mbar) can be separated from one another. However, this distillation is performed under reduced pressure.

A purely distillative process is no longer suitable for the ammoximation of macrocyclic ketones, such as cyclododecanone. The separation of a ketone and an oxime by distillation becomes increasingly more difficult with increasing ring size. Moreover, the high distillation temperatures, even under a high vacuum, required for such a process result in considerable decomposition. Therefore, cyclododecanone oxime can not be distilled without decomposition.

In Example 1 of EP 0 208 311, Montedipe describes the reaction and work-up of the ammoximation of cyclohexanone without alcohol as a solvent in a three-phase mixture (organic-aqueous-solid) comprising cyclohexanone as the organic phase, 32% strength by weight aqueous ammonia and 32% strength by weight hydrogen peroxide as aqueous phase, and pulverulent titanium silicalite as a solid catalyst. A disadvantage of this process is that the organic phase consisting of cyclohexanone oxime and unreacted cyclohexanone crystallizes out of the reaction mixture on cooling and thus encapsulates the catalyst. Therefore, to work up and separate off the catalyst, the organic phase has to be redissolved in toluene and the aqueous phase has to be extracted a number of times with toluene. This process may well be suitable for batchwise operations in the laboratory, but the process cannot be converted into a continuous industrial process. Even if this process were converted into a continuous process, it would require a complicated apparatus, which is as of yet, not available.

Montedipe in U.S. Pat. No. 4,794,198 (corresponds to EP 0 267 362) mention, in passing, that work-up by extraction is possible where water-miscible solvents, for example aqueous tertbutanol, are used as solvent in the ammoximation. In this method, a suitable organic solvent is added to the reaction mixture at the end of the reaction and the oxime is subsequently separated from the aqueous solvent by addition of an organic solvent. In batchwise experiments, the reaction mixture was cooled, diethyl ether was added to the resulting suspension (Examples 3 and 20), the catalyst was subsequently filtered off, and the organic phase was decanted off. In continuous experiments using a catalyst suspension (Example 32) and in a trickle bed (Example 33), no details of the work-up are given.

The European patent application EP 0 267 362 (Montedipe) claims not only the reaction of cyclohexanone but also the reaction of some other carbonyl compounds such as cyclododecanone. However, no concrete example using cyclododecanone is reported.

A continuous ammoximation process is described by Enichem in EP 0 496 385. After isolation of the catalyst, an ammonia-containing azeotrope of tert-butanol and water is separated off from the reaction mixture in a first column (denoted by C1). The remaining reaction mixture consisting of cyclohexanone oxime (m.p. 95° C.), further secondary components, and residual water collects at the bottom of this column. The oxime is subsequently washed out of the reaction mixture by addition of toluene to the extractor. claim 8 of EP 0 496 385, makes specific mention of the carbonyl compounds acetone, cyclohexanone, methyl ethyl ketone, acetophenone, cyclododecanone and enanthaldehyde. However, the process is applied only to cyclohexanone in the reported Examples 1–5.

The difficulty occurring in the work-up process described for large ketone oximes, for example cyclododecanone oxime, is that the oxime is only sparingly soluble in water and the melting point of the oxime is above the boiling point of water. Accordingly, the work-up process described in EP 0 496 385 has only limited suitability for oximes larger than cyclohexanone oxime, or is not suitable at all. When we repeated this procedure using cyclododecanone, cyclododecanone oxime crystallized out in the stripping section of the column in every case.

SUMMARY OF THE INVENTION

Accordingly, it is an object of the present invention to provide a continuous work-up process for the ammoximation of ketones, in particular large cycloalkanones having 8–20 carbon atoms, in which the catalyst is separated off after the reaction, the oxime is isolated from the reaction mixture, the water of reaction is separated from the solvent, and the remaining alcohol is returned to the process, without the product precipitating as solid during these steps of the work-up process.

The above object highlights certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

DETAILED DESCRIPTION OF THE INVENTION

Unless specifically defined, all technical and scientific terms used herein have the same meaning as commonly understood by a skilled artisan in organic chemistry. "Working up" is understood in the art to mean a method of isolation and/or purification of a desired product subsequent to a reaction.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The present invention is based in part on the Inventor's surprising discovery that ammoximation products of ketones can be worked up using a ternary solvent system which comprises (a) one or more liquids which are completely miscible or readily miscible with water (e.g., alcohol), (b) water, and (c) an organic solvent which is only partly miscible with water and alcohol and whose boiling point is above the boiling points of the alcohol and water. Further, by exploiting the miscibility gap of the ternary solvent system by varying the water content and taking the composition (of the aqueous-alcoholic phase) above the distillation limit line extraction can be accomplished. Alternatively, a plurality of extraction stages can also be used.

A preferred embodiment of the present invention is a process for working up an ammoximation reaction mixture of a ketone, by (1) separating a catalyst from the reaction mixture, (2) removing the ketone oxime product with at least one liquid-liquid extraction in a ternary solvent system, (3) discharging the water of the reaction, and (4) recirculating a solvent in the reaction mixture. The ammoximation reaction mixture of a ketone in this embodiment is obtained by ammoximation of a ketone with hydrogen peroxide and ammonia in homogeneous solution over a titanium-containing catalyst. In one embodiment of the present invention, the process is continuous.

Figure 1:
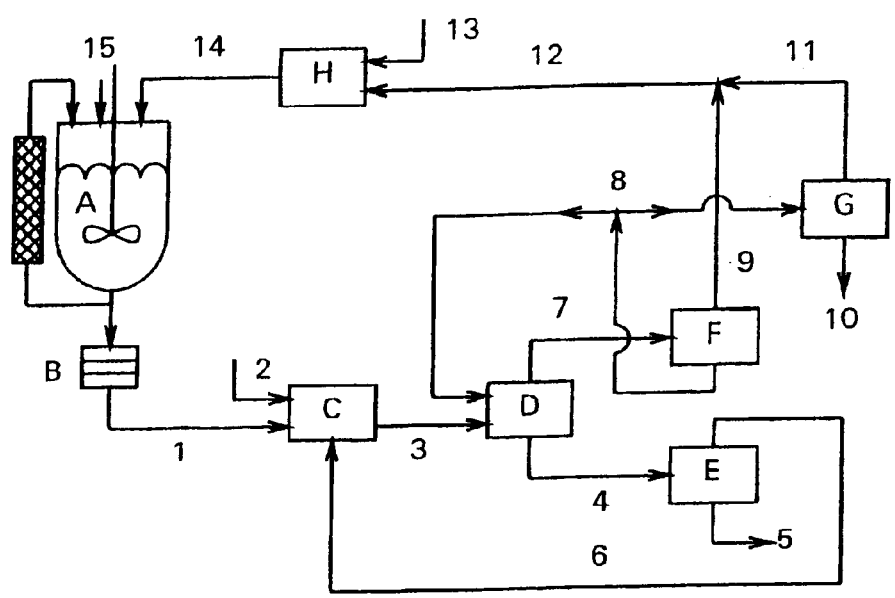
FIG. 1: General outline of the process of the present invention. It is based on the miscibility gap, which exists between an alcohol-aqueous phase and a nonpolar hydrocarbon.

According to the present invention, after the reaction is completed the catalyst is removed from the reaction mixture. If a titanium silicalite catalyst is used in powder form in reactor A, it is removed in a subsequent separation step B. A suitable apparatus for industrial use in such a step include a filter candle, a pressure filter, and a filter centrifuge. However, catalyst removal becomes unnecessary if a circulation reactor (A) with shaped catalyst bodies is used as a fixed bed (see FIG. 1). In this instance, a purification filter is used as separation step B to prevent any solid impurities, spent particles, or abraded material from contacting the shaped bodies which may be present in the reaction mixture.

Following catalyst removal, the reaction mixture (1) comprises the respective ketone oxime completely dissolved in an alcohol having from 1 to 6 carbon atoms, which is readily or completely miscible with water and the water that has been introduced into and/or formed in the reaction. Examples of suitable alcohols include methanol, ethanol, n-propanol, isopropanol, tert-butanol and amyl alcohol; or a mixture thereof. The solution further comprises unreacted ammonia and possibly traces of unreacted hydrogen peroxide, unreacted starting material (ketone), and by-products and impurities present in the starting material. The latter may include the imine analogous to the respective oxime. By using technical-grade cyclododecanone as the ketone, the amounts of secondary components and impurities present are low, generally significantly less than 1 weight % based on the ketone used.

The reaction mixture (1) is then mixed with a defined amount of a nonpolar extractant (2) in a mixer, taking care to ensure that the amount of extractant added has sufficient solvent capability for the product (oxime) at the chosen extraction temperature in the extractor/separator D. The resulting ternary solvent system, therefore, comprises solvent, water, and an extractant. Nonpolar hydrocarbons are the preferred extractant and may be an aliphatic or a cycloaliphatic hydrocarbon; or a mixture thereof. It is particularly preferred that the nonpolar hydrocarbon selected have a boiling point greater than the boiling point of water and the alcohol selected for the reaction. Examples of the nonpolar hydrocarbon include ethylcyclohexane, dimethylcyclohexane, isopropylcyclohexane, hexahydrocumene, tert-butylcyclohexane, cycloheptane, cyclooctane, cyclononane, cyclodecane, cycloundecane, cyclododecane, alkylated ethylcyclohexane, alkylated dimethylcyclohexane, alkylated isopropylcyclohexane, alkylated hexahydrocumene, alkylated tert-butylcyclohexane, alkylated cycloheptane, alkylated cyclooctane, alkylated cyclononane, alkylated cyclodecane, alkylated cycloundecane, and alkylated cyclododecane, preferably those having alkyl chains containing from 1 to 6 carbon atoms.

Figure 2:
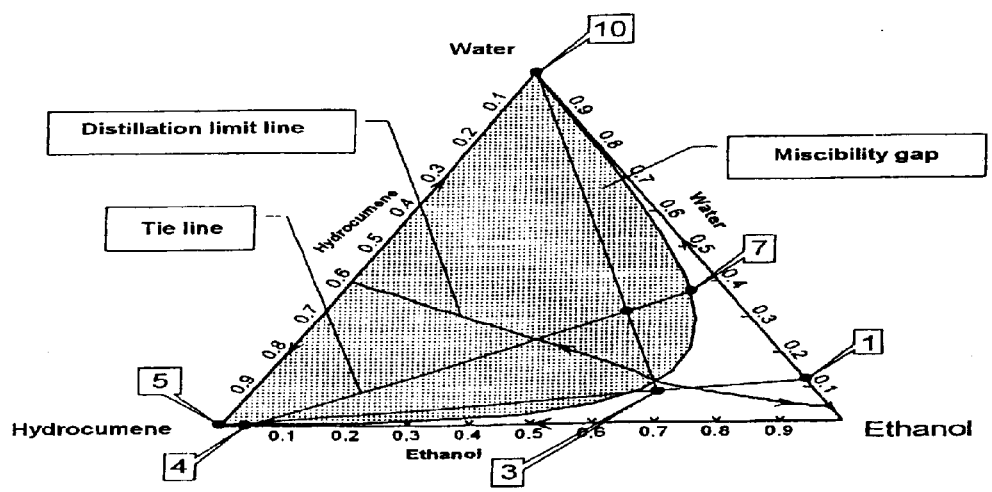
FIG. 2: The miscibility gap for the ternary system of ethanol, water, and hexahydrocumene. The details are for a constant pressure of 1.013 bar. The temperature is different at every point of the diagram and corresponds to the boiling point at the respective composition and a total pressure of 1.013 bar. The figures shown are mass fractions.

In the process of the invention, the mixture (3) is kept at a temperature of 60 to 90° C. under atmospheric pressure or a superatmospheric pressure as dictated by the solvent employed. At this temperature, the mixture is still present as a single phase without crystallization of the oxime. A two-phase region in extractor D can be achieved by varying the parameters (temperature, pressure) or by addition of circulated water (8). Accordingly, the mixture separates along the tie lines into two mutually immiscible solutions (4) and (7), without crystallization of oxime, as shown in FIG. 2.

The oxime reaction product, and sometimes the unreacted ketone, or secondary components, may completely or almost completely enter a lipophilic phase (4). This separation step D (addition of circulated water, phase separation) can be optimized in process engineering terms by employing suitable extractors, for example a countercurrent extractor. It is possible to use all customary types of extractor, which include a mixer-settler cascade, a centrifugal extractor, and a cascade of centrifugal extractors. The extractor can be operated either in crosscurrent or in countercurrent. Should traces of oxime remain in the alcoholic phase (7) after the main separation step D, they can be washed out of stream (7) in a downstream scrubbing step (not shown explicitly) using fresh a extractant. The extractant used here is subsequently employed further as stream (2) in separation step D.

Residual traces of alcohol and water are removed from the product stream (4) by a subsequent purification step E. Suitable purification steps include a short distillation column or a stripper. The substream (6), which comprises residual ammoniacal alcohol, water, and a small amount of the nonpolar hydrocarbon, is recirculated to the reactor A. Alternatively, substream (6) may be recirculated directly to the mixer C. To keep the organic phase (5) free of alcohol and ammonia it is important to provide a downstream purification step E. Solution (5) contains the ketone oxime in an aliphatic or cycloaliphatic hydrocarbon. In addition, the solution contains traces of starting material (ketone) and possibly by-products of the ammoximation. The oxime can be extracted directly from this solution by addition of concentrated sulfuric acid and be used for the Beckmann rearrangement. Therefore, the downstream purification step E is necessary to suppress the formation of dialkyl sulfates and ammonium sulfate in the typical subsequent reaction step for the oximes (i.e., the Beckmann rearrangement in concentrated sulfuric acid).

The aqueous-alcoholic phase (7) from the separation stage D can be separated into its constituents by downstream, single-stage or multistage distillation. Generally, the preferred short-chain alcohols have a boiling point less than that of water and are removed as an azeotrope (9, 11). The short-chain alcohols are subsequently combined (12), admixed with fresh ketone (13) (apparatus H) and returned to the ammoximation reactor (14), where the mixture is admixed with hydrogen peroxide, ammonia and, if appropriate, fresh titanium silicalite (summarized as stream (15)).

Energetically, it is favorable to perform the separation of stream (7) into alcohol and water in two or more separation stages (F and G). The bottom layer (8) from the first, rough step F contains water and alcohol up to 20% by weight. The major part of this mixture is returned as a circulated water stream to the extractor D. Only a substream corresponding to the amount of water formed during the ammoximation reaction, or introduced into the reactor A in the aqueous hydrogen peroxide and ammonia (15), is completely freed of alcohol in a downstream column G and discharged as wastewater (10).

The work-up sequences D and E can be combined in an extraction column, with the actual extraction step D occurring near the inlet of the column. At the bottom of the extraction column, stream (5) can be directly removed and passed to a further reaction, while stream (7) is taken off the top and subsequently fractionated in the distillation stages F and G. Deposition of oxime is avoided by sufficient runback of condensed extractant into the extraction column. The extraction is preferably performed at a temperature of 0 to 130° C. and a pressure of 0.1 to 10 bar.

The steps/conditions described above for the use of alcohols, which are readily or completely miscible with water, may also be employed for other organic liquids, which are readily or completely miscible with water and are inert under the reaction conditions.

The novel principle of the work-up is shown in FIG. 2 for the ternary system ethanol, water and hexahydrocumene (abbreviated to hydrocumene in the figure). The compositions of these three components in the streams (1), (3), (4) and (7) are marked. The dotted area indicates the two-phase region. After addition of hexahydrocumene to the mixer C, the system initially remains in the single-phase region (3). Addition of circulated water in the extractor D, in a regulated manner, results in the formation of a two-phase region. Accordingly, the system separates along the tie lines into the two mutually immiscible phases (4) and (7), with the composition of the phase (7) being above the distillation limit line. Purification by downstream distillation columns subsequently occurs along the distillation lines.

The terms "readily miscible" and "partly miscible" as used herein can be interpreted in view of the following and as defined by Römpp's Chemical Encyclopedia (9$^{th}$ Expanded and Revised Edition 1989, p. 2805). Compounds may be miscible with one another over a broad range of proportions based on the miscibility gap between the compounds. For example, the miscibility gap between two liquids A and B is defined as follows: A is miscible in B within the limits of 100%–x % and y %–0%, where A+B= 100%. A miscibility gap exists between x % and y %.

In the present application, solvent (a) is "readily miscible" with water. If a miscibility gap exists, it is small: x>25%, y<75%.

In the present application, solvent (c) is "partly (i.e., poorly) miscible" with water. In this scenario, the miscibility gap is characterized by x<25%, y>75%.

For additional insight into the intricacies of miscibility the artisan is directed to Godfrey's subdivision into mixture classes discussed in Rompp's Chemical Encyclopedia (p2805).

Numerous modifications and variations on the present invention are possible in light of the above teachings. It is therefore, to be understood that within the scope of the accompanying claims, the invention may be practiced otherwise than as specifically described herein.

The present application claims priority to German Application No. DE 101 42 621.6, filed on Aug. 31, 2001, which is hereby incorporated by reference in its entirety.

What we claim is:

1. A process for working up an ammoximation reaction mixture of a ketone, which comprises separating a catalyst from the reaction mixture, removing a ketone oxime product with at least one liquid-liquid extraction in a ternary solvent system, discharging the water of the reaction, and recirculating a solvent in the reaction mixture.

2. The process according to claim 1, wherein the an ammoximation reaction mixture of a ketone comprises ammoximating a ketone with hydrogen peroxide and ammonia in a homogeneous solution over a titanium-containing catalyst.

3. The process according to claim 1, wherein the catalyst is a titanium silicalite powder.

4. The process according to claim 1, wherein the solvent in the reaction mixture is a polar organic liquid, which is miscible with water.

5. The process according to claim 1, wherein the solvent in the reaction mixture comprises one or more short-chain alcohols selected from the group consisting of methanol, ethanol, n-propanol, isopropanol, tert-butanol, and amyl alcohol.

6. The process according to claim 1, which is continuous.

7. The process according to claim 1, wherein the ternary solvent system comprises a solvent, water, and an extractant.

8. The process according to claim 7, wherein the extractant is a nonpolar hydrocarbon, which has a boiling point greater than the boiling point of water or the solvent.

9. The process according to claim 7, wherein the extractant is selected from the group consisting of ethylcyclohexane, dimethylcyclohexane, isopropylcyclohexane, hexahydrocumene, tert-butylcyclohexane, cycloheptane, cyclooctane, cyclononane, cyclodecane, cycloundecane, cyclododecane, alkylated ethylcyclohexane, alkylated dimethylcyclohexane, alkylated isopropylcyclohexane, alkylated hexahydrocumene, alkylated tert-butylcyclohexane, alkylated cycloheptane, alkylated cyclooctane, alkylated cyclononane, alkylated cyclodecane, alkylated cycloundecane, and alkylated cyclododecane.

10. The process according to claim 7, further comprising separating the extractant from a residual hydrophilic solvent.

11. The process according to claim 1, wherein the liquid-liquid extraction solvent is a nonpolar liquid, which is immiscible miscible with water.

12. The process according to claim 1, wherein the liquid-liquid extraction comprises a stream of circulated water.

13. The process according to claim 1, wherein the liquid-liquid extraction is carried out at a temperature of 0 to 130° C. and a pressure of 0.1 to 10 bar.

14. The process according to claim 1, wherein the ketone is selected from the group consisting of cyclooctanone, cyclodecanone, cyclododecanone, cyclopentadecanone and acetophenone.

15. The process according to claim 1, wherein the discharged water of the reaction is recirculated.

* * * * *